United States Patent
Zhang et al.

(10) Patent No.: US 9,617,227 B2
(45) Date of Patent: Apr. 11, 2017

(54) PROCESS OF PREPARING A QUINAZOLINE DERIVATIVE

(71) Applicant: ScinoPharm (Changshu) Pharmaceuticals, Ltd., Changshu, Jiangsu Province (CN)

(72) Inventors: Xiaoheng Zhang, Changshu (CN); Xizhou Lv, Changshu (CN)

(73) Assignee: SCINOPHARM (CHANGSHU) PHARMACEUTICALS, LTD., Changshu (CN)

( * ) Notice: Subject to any disclaimer, the term of this patent is extended or adjusted under 35 U.S.C. 154(b) by 0 days.

(21) Appl. No.: 14/888,008

(22) PCT Filed: Jun. 10, 2014

(86) PCT No.: PCT/CN2014/079620
§ 371 (c)(1),
(2) Date: Oct. 29, 2015

(87) PCT Pub. No.: WO2015/188318
PCT Pub. Date: Dec. 17, 2015

(65) Prior Publication Data
US 2016/0200688 A1   Jul. 14, 2016

(51) Int. Cl.
*C07D 239/94* (2006.01)

(52) U.S. Cl.
CPC ............... *C07D 239/94* (2013.01)

(58) Field of Classification Search
None
See application file for complete search history.

(56) References Cited

U.S. PATENT DOCUMENTS 5,770,599 A   6/1998   Gibson

FOREIGN PATENT DOCUMENTS

| CN | 100420676 C | | 9/2008 |
|---|---|---|---|
| CN | 101402610 A | | 4/2009 |
| CN | 101638398 | * | 8/2009 |
| CN | 102146060 A | | 8/2011 |
| CN | 103755648 | * | 12/2013 |
| IN | 901/CHE/2006 | | 6/2006 |
| IN | 219/CHE/2005 | | 3/2007 |
| IN | 236840 B | | 12/2009 |
| WO | 96/33980 A1 | | 10/1996 |

OTHER PUBLICATIONS

Chandregowda, Venkateshappa. Convergent Approach for Commercial Synthesis of Gefitinib and Erlotinib. Org. Process Res. Dev. 2007, 11(5), 813-816.*

* cited by examiner

*Primary Examiner* — Samantha Shterengarts
(74) *Attorney, Agent, or Firm* — Enshan Hong; VLP Law Group LLP

(57) ABSTRACT

A concise, efficient and cost- and time-saving process for the preparation of a quinazoline derivative of formula A given below:

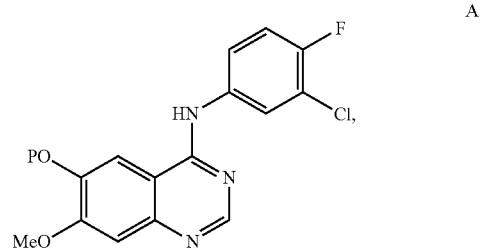

which is an intermediate for making gefitinib or gefitinib itself, comprising reacting a compound of Formula B:

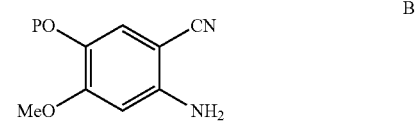

with 3-chloro-4-fluoroaniline (VI) in the presence of a N,N-dialkyl formamide acetal, a Bronsted acid catalyst, and a solvent in a one-pot reaction.

13 Claims, No Drawings

PROCESS OF PREPARING A QUINAZOLINE DERIVATIVE

BACKGROUND OF THE INVENTION

1. Field of the Invention

The present invention relates to an improved process for the preparation of an intermediate useful for the manufacture of gefitinib. In particular, the present invention relates to a chemical process for the preparation of a quinazoline derivative of formula A given below:

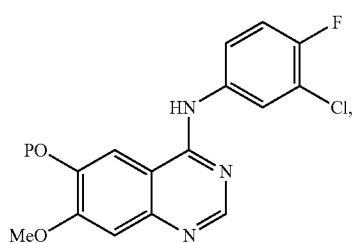

where P represents a hydrogen, 3-(morpholinyl)propyl or a hydroxyl-protecting group.

2. Description of the Related Art

Gefitinib is an anilinoquinazoline with the chemical name N-(3-chloro-4-fluorophenyl)-7-methoxy-6-[3-(morpholin-4-yl)propoxy]quinazolin-4-amine and the following structural formula I:

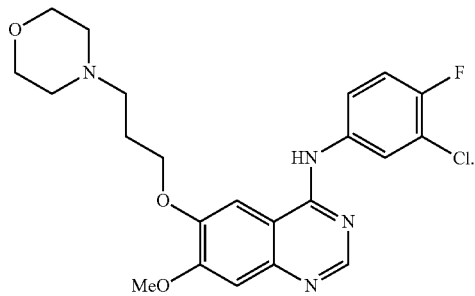

Gefitinib is marketed with a brand name of IRESSA by AstraZeneca Pharmaceuticals LP, indicated as monotherapy for continued treatment of patients with locally advanced or metastatic non-small cell lung cancer after failure of both platinum-based and docetaxel chemotherapies who are benefiting or have benefited from IRESSA (gefitinib).

Gefitinib is the first selective inhibit of epidermal growth factor receptor's (EGFR) tyrosine kinase domain. It was first disclosed in International Patent Application No. WO 96/33980 and U.S. Pat. No. 5,770,599. The process disclosed is depicted in the following scheme 3. The process of preparing gefitinib disclosed in this patent application involves using methanesulfonic acid and L-methionine in the selective demethylation of 6,7-dimethoxy-3H-quinazolin-4-one to obtain the 6-hydroxyl derivative. Afterwards, the hydroxyl moiety is protected by acylating the 6-hydroxyl moiety, followed by reacting the 6-acylated derivative with thionyl chloride to obtain the chloro derivative, which is then condensed with 3-chloro-4-fluoroaniline. The resulting intermediate is hydrolyzed, and then etherified with 3-morphorlinopropyl chloride to give crude gefitinib which is further purified by column chromatography.

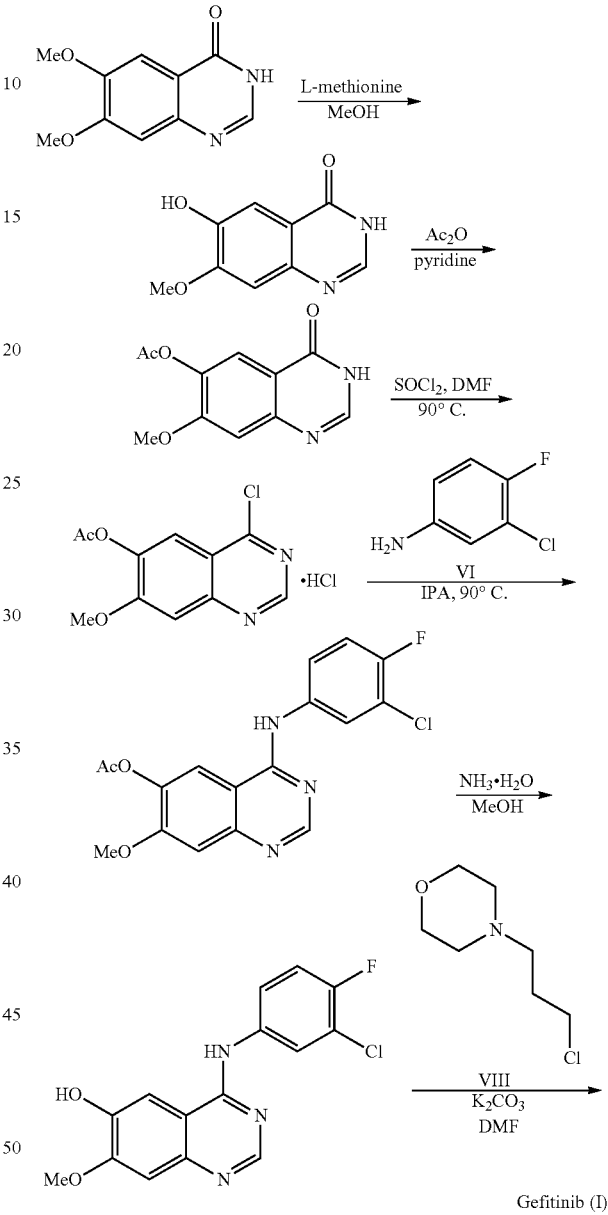

With regard to the above process, the intermediate of Formula VII was prepared from 6,7-dimethoxyquinazolin-4(3H)-one through five steps, containing selective removal of methyl group at C6 with L-methionine in the presence of methane sulfonic acid, acetylation, chlorination, $S_NAr$ reaction and deacetylation. Such a process suffers from several disadvantages in the preparation of gefitinib. One of the major disadvantages is that it involves removing methyl group of the starting material at C7 by the use of methane sulfonic acid and L-methionine in demethylation step. The selective demethylation results in the formation of isomeric impurities, which has to proceed with further purification, such as column chromatography, in the manufacture of gefitinib. The process also involves the use of thionyl chloride for chlorination in the manufacture of gefitinib. However, thionyl chloride is not environmentally friendly and is difficult to handle.

Indian Patent Application No. IN2005CH00219 reports a method of synthesizing 6-hydroxy-7-methoxy quinolin4-(3H)-one, and another method of converting 6-hydroxy-7-methoxy quinolin4-(3H)-one to gefitinib through an intermediate of formula VII. The process reported is depicted in the following scheme 4. Specifically, the process involves using a compound of formula IV to prepare the intermediate of formula VII useful for the preparation of gefitinib via passing through the intermediates of formulae XI-XIV as shown below. However, the process has a major disadvantage, in the preparation of the intermediate of formula VII, which is still not concise enough because the cyclization of reacting 4,5-substituted 2-amino-benzamide (XI) with HCOOH to give the quinazolin-4-one of formula XII results in the subsequent long-winded steps in the preparation of the intermediate of formula VII.

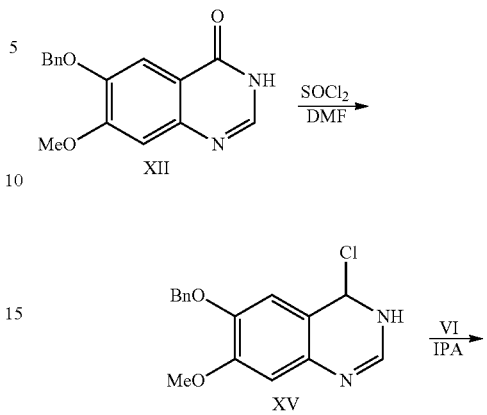

Scheme 5 - The process disclosed in CN100420676C

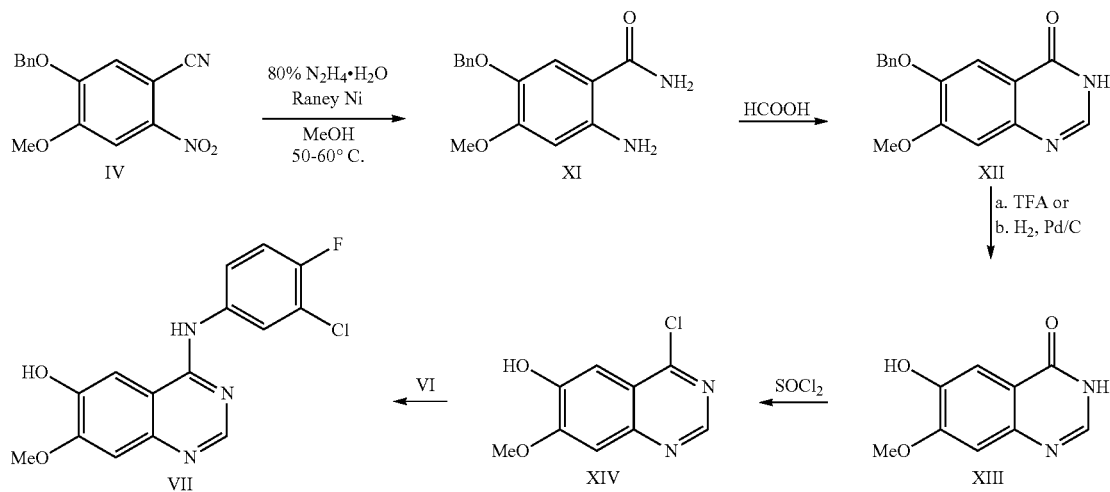

Scheme 4 - The process disclosed in IN2005CH00219

Chinese Patent No. CN100420676C discloses a process for preparing the intermediate of formula VII useful for the manufacture of gefitinib. The process disclosed in CN100420676C is depicted in the following scheme 5. The process involves the use of 6,7-substituted quinazolin-4-one (XII) in the preparation of the intermediate of formula VII via passing through intermediates of formulae XV and X as shown below. In comparison with the process disclosed in IN2005CH00219, the process merely changes chemical reaction orders of synthesizing the compound of formula VII beginning with the compound of formula XII. Thus, the number of reaction steps is not reduced at all. Although this patent does not report how to obtain the compound of Formula XII, it is very likely that the compound of Formula XII could be obtained from the compound of formula IV from a chemical perspective. Therefore, this process does not provide a more efficient synthetic route to remedy the drawback of the process disclosed in IN2005CH00219.

-continued

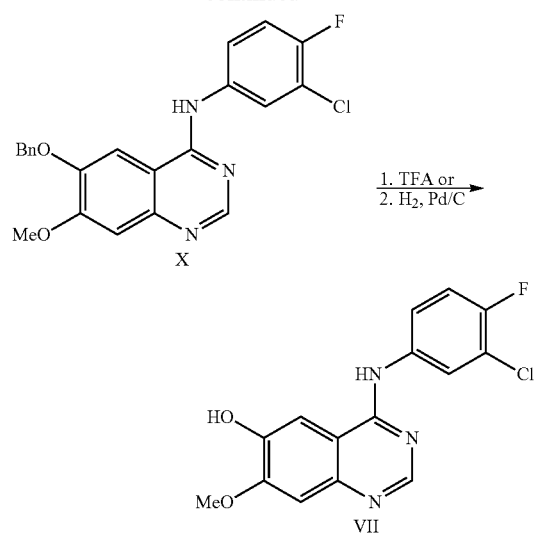

Indian Patent Application No. IN2006CH00901 reports a process for the synthesis of gefitinib. The process disclosed in IN2006CH00901 is depicted in the following scheme 6. This process principally involves converting the compound of formula XVI into an oxime and dehydrating of the oxime to obtain the compound of formula XVII, followed by proceeding with the reactions of nitration, reduction and amidine formation to obtain the compound of formula XX, and then the compound of formula XX is isolated as an oily intermediate by evaporation for the preparation of gefitinib. Although the process disclosed in this patent application is a more efficient process for the synthesis of gefitinib because of the reduction of the number of steps, there is a significant drawback that all intermediates must be isolated in the processing procedure. It is not beneficial in terms of cost and time.

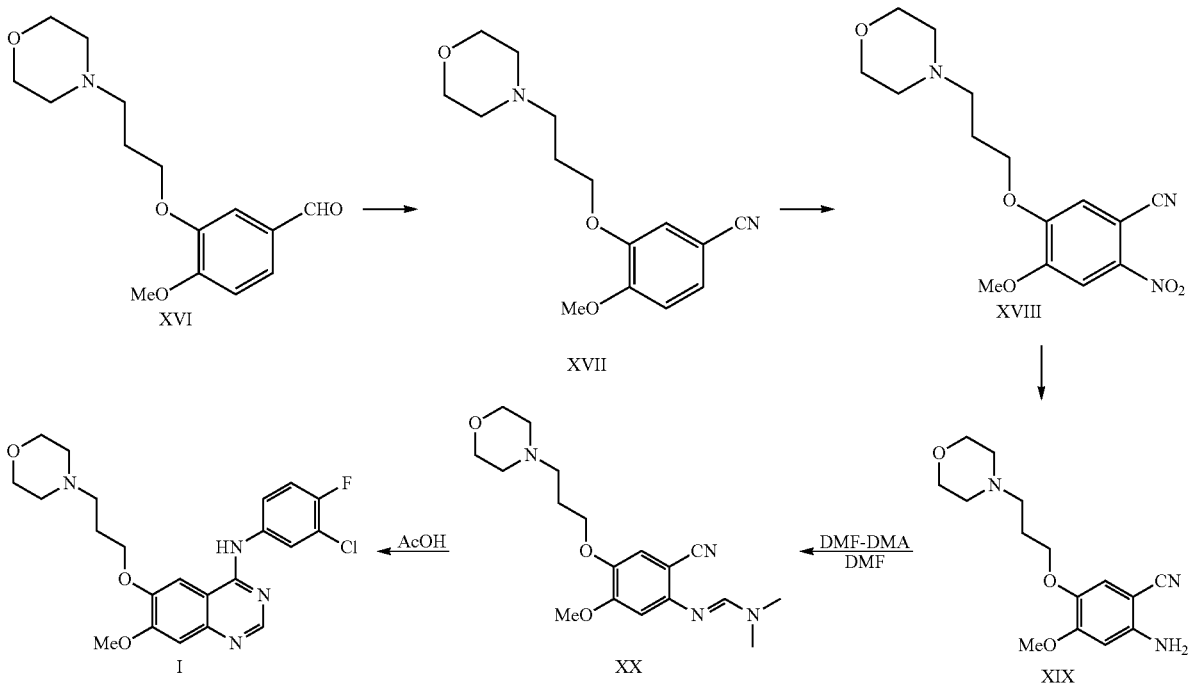

Chinese Patent Application No. CN101402610A discloses a synthesis of gefitinib. The process disclosed in CN101402610A is depicted in the following scheme 7. The process involves a cyclization of a compound of formula XIX with a compound of formula XXI prepared from 3-chloro-4-fluoroaniline to synthesize gefitinib. However, this process still needs to isolate the compound of formula XXI first before reacting with the compound of formula XIX. That is a more complicated procedure.

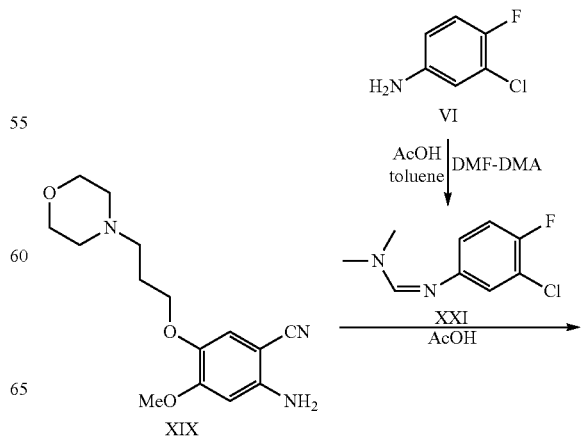

-continued

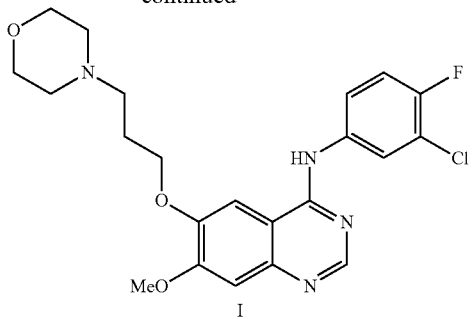

Given the above, there is a need for a more direct and less laborious process for preparing the intermediate of formula VII useful for the manufacture of gefitinib.

SUMMARY OF THE INVENTION

The present invention is related to a process for the preparation of a quinazoline derivative of formula A shown below, wherein P is hydrogen, 3-(morpholinyl)propyl or a hydroxyl-protecting group:

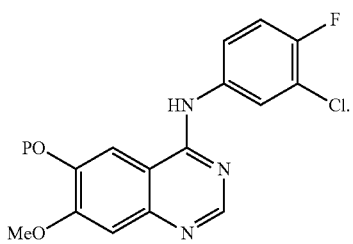

The process in accordance with the present invention comprises a one-step cyclization of a compound of formula B or its salt:

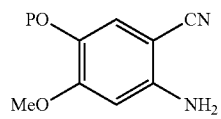

with 3-chloro-4-fluoroaniline (VI) in preparing the quinazoline derivative of formula A.

Specifically, the first aspect of the present application is a process for the preparation of the compound of formula A, which comprises reacting a compound of formula B or its salt:

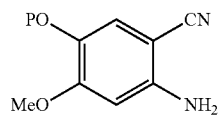

with 3-chloro-4-fluoroaniline (VI) in the presence of a N,N-dialkyl formamide acetal, a Brønsted acid catalyst, and a solvent.

The second aspect of the present application is a process of making gefitinib or a pharmaceutically acceptable salt thereof, which comprises:
reacting a compound of Formula B:

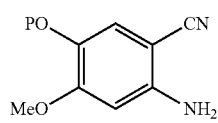

or its salt with 3-chloro-4-fluoroaniline (VI) in the presence of a N,N-dialkyl formamide acetal, a Brønsted acid catalyst, and a solvent to prepare the compound of formula A show above;
converting the compound of formula A to gefitinib or its pharmaceutically acceptable salt thereof.

The compound of formula A can be converted to gefitinib by any suitable method, e.g., a method that has been disclosed in a publication. For example, the compound of formula A can be converted to gefitinib by nucleophilic substitution reaction of hydroxyl group with 4-(3-chloropropyl) morpholine or 4-(3-bromopropyl) morpholine, and if necessary, deprotection of hydroxyl-protection group by any suitable method prior to nucleophilic substitution reaction. Preferably, the compound of formula A without a hydroxyl-protection group, i.e. P is a hydrogen, can be converted to gefitinib by reacting the compound of formula A with 4-(3-chloropropyl)morpholine (VIII) to form gefitinib.

The major advantage of the present invention is to provide a concise and efficient process for preparing a quinazoline derivative of formula A which is a key intermediate and can be used to manufacture gefitinib.

DETAILED DESCRIPTION OF THE PRESENTLY PREFERRED EMBODIMENTS

As used herein, the term "hydroxyl-protecting group" refers to any suitable group that can protect the hydroxyl group on a compound (e.g., compound of formula A) from unwanted reaction. The general hydroxyl-protecting group is disclosed in the publication *Greens Protective Groups in Organic Synthesis* (Perter G. M. WuTs and Theodora W. Greene, John Wiley & Sons, Inc. 4$^{th}$ Edition, 2007). For example, the hydroxyl protecting group can be an acyl, alky, phenyl, substituted phenyl, benzyl, or substituted benzyl group, preferably a methyl, benzyl, or p-methoxylbenzyl group.

N,N-dialkyl formamide acetal discussed herein is preferably N,N-dialkyl formamide acetal having a formula

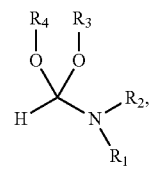

wherein, $R_1$, $R_2$, $R_3$, $R_4$ is independently an alkyl containing 1-10 carbon atoms, more preferably N,N-dimethylformamide dimethylacetal.

As used herein, the term "Brønsted acid catalyst" refers to an acid being able to lose, or "donate" a proton and catalyze a reaction by proton transfer, for example, acetic acid, fumaric acid, malic acid, tartaric acid, citric acid, maleic acid, and trifluoroacetic acid, preferably acetic acid (AcOH) and trifluoroacetic acid (TFA)

As used herein, the term "solvent" refers to a liquid substance that dissolves a solute resulting in a solution, for example, acetic acid, N,N-dimethylacetamide, N-methyl-2-pyrrolidone (NMP), N,N-dimethylformamide, toluene (PhMe), methanol (MeOH), acetonitrile (ACN), ethyl acetate (EtOAc), tetrahydrofuran (THF), dimethylsulfoxide (DMSO), dichloromethane (DCM), acetone, preferably acetic acid (AcOH), toluene (PhMe), methanol (MeOH), acetonitrile (ACN), ethyl acetate (EtOAc), tetrahydrofuran (THF), N-methyl-2-pyrrolidone (NMP), and N,N-dimethylformamide (DMF).

The present application relates to a process for the preparation of a quinazoline derivative of formula A useful for the manufacture of gefitinib, which comprises a one-step cyclization of an ortho-amino-benzonitrile derivative with 3-chloro-4-fluoroaniline (VI) to produce the quinazoline derivative of formula A.

In accordance with one embodiment of the present application, the process involves reacting 2-amino-5-hydroxy-4-methoxybenzonitrile (V) with 3-chloro-4-fluoroaniline (VI) in a one-step reaction to prepare 4-(3-chloro-4-fluorophenyl amino)-7-methoxyquinazolin-6-ol (VII).

In accordance with another embodiment of the present application, the process involves reacting 2-amino-5-benzyloxy-4-hydroxyl-benzonitrile (IX) with 3-chloro-4-fluoroaniline (VI) in a one-step reaction to prepare 4-(3-chloro-4-fluorophenyl amino)-6-benzyloxy-7-methoxyquinazoline (X).

According to one embodiment of the present application, there is provided a process for the preparation of 4-[(3-chloro-4-fluorophenyl) amino]-7-methoxyquinazolin-6-ol (VII) (see Scheme 1), comprising: 3-hydroxy-4-methoxybenzonitrile (II) is benzylated to give 3-(benzyloxy)-4-methoxybenzonitrile (III). The compound of formula III is nitrated to give 5-(benzyloxy)-4-methoxy-2-nitrobenzonitrile (IV, See U.S. Pat. No. 6,048,864). Subsequently, the compound of formula IV is hydrogenated to give 2-amino-5-hydroxy-4-methoxybenzonitrile (V) in the presence of Pd/C, and then the compound of formula V is cyclized with 3-chloro-4-fluoroaniline (VI) in the presence of N,N-dimethylformamide dimethylacetal (DMF-DMA) and acetic acid (AcOH) to give 4-(3-chloro-4-fluorophenyl amino)-7-methoxyquinazolin-6-ol (VII). The compound of formula (VII) can be converted to gefitinib via a substitution reaction with 4-(3-chloropropyl)morpholine (VIII).

Scheme 1 - A process for the preparation of the compound of formula VII applied to the manufacture of gefitinib

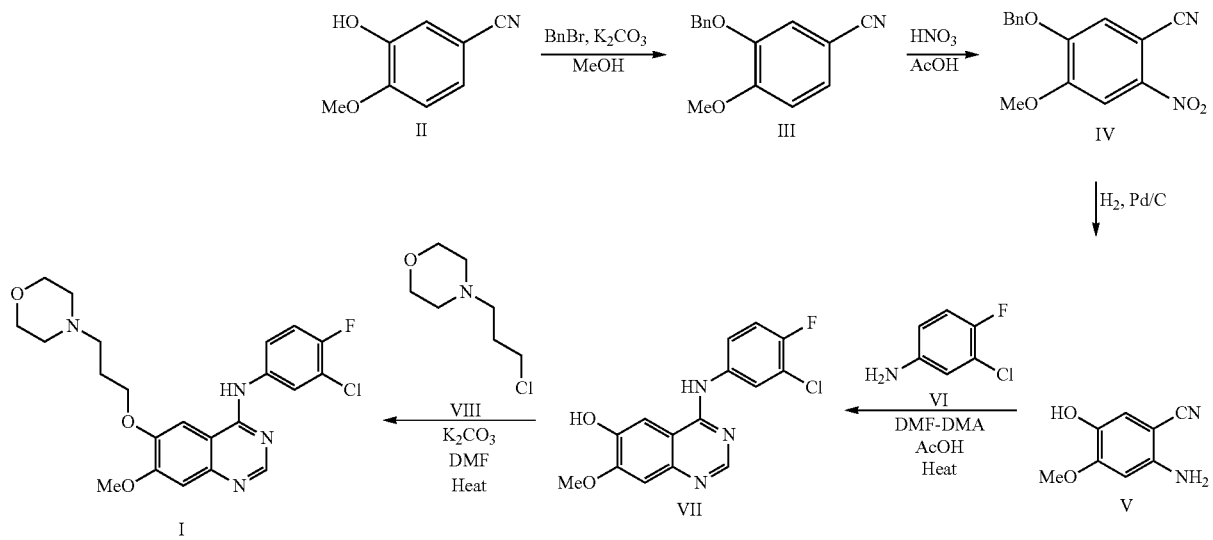

In accordance with another embodiment of the present application, the compound of formula IV is reduced into 2-amino-5-benzyloxy-4-hydroxyl-benzonitrile (IX) with sodium dithionite (see Scheme 2). The compound of formula IX is cyclized with 3-chloro-4-fluoroaniline (VI) in the presence of N,N-dialkyl formamide acetal, e.g., N,N-dimethylformamide dimethylacetal (DMF-DMA), a Brønsted acid catalyst, and/or a solvent, e.g., acetic acid (AcOH) and trifluoroacetic acid (TFA) to give 6-(benzyloxy)-4-(3-chloro-4-fluorophenylamino)-7-methoxyquinazoline (X), and then the compound of formula X is debenzylated with trifluoacetic acid (TFA) to give Formula VII.

Scheme 2 - An embodiment for the preparation of the compound of formula VII

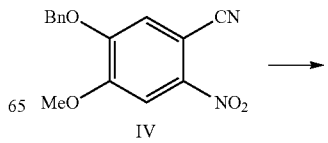

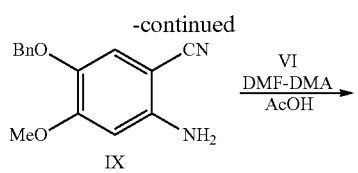

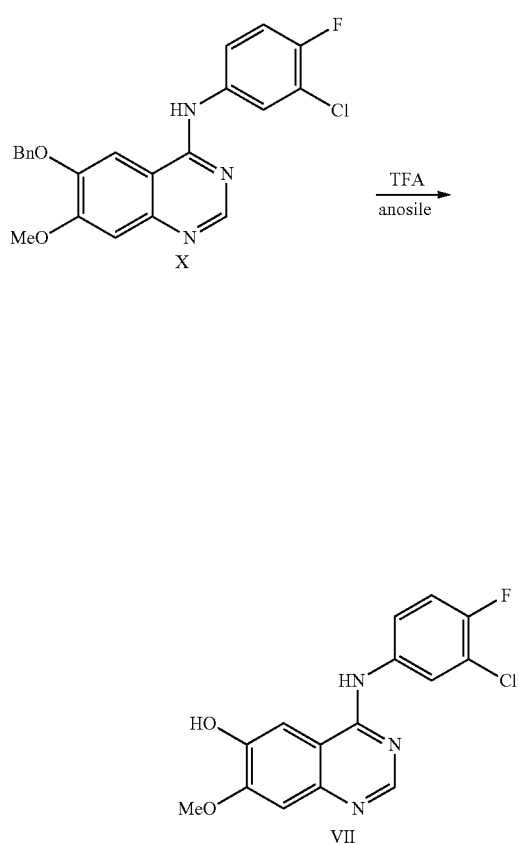

In accordance with another embodiment of the present application, a process for preparing the compound of formula VII comprises conducting the amidine formation and cyclization steps in a one-step reaction. The advantage of the one-step reaction is that there is no need to isolate any intermediates when involving the reaction of the compound of formula V and 3-chloro-4-fluoroaniline (VI) in the preparation of the intermediate of formula VII. Actually, several processes for preparing gefitinib are described in the literature but those processes involve multiple steps and hence are consuming. The inventors of the present invention surprisingly noted that either between the compounds of formula VI and XXI or the compounds of formula V and XXII, in the presence of a cyclization reagent N,N-dialkyl formamide acetal, e.g., DMF-DMA, and a Brønsted acid catalyst, e.g., acetic acid (AcOH) and trifluoroacetic acid (TFA), and a solvent, e.g., acetic acid (AcOH), toluene (PhMe), methanol (MeOH), acetonitrile (ACN), ethyl acetate (EtOAc), tetrahydrofuran (THF), and N-methyl-2-pyrrolidone (NMP), at a lifted temperature, preferably at the range of 20-100° C., more preferably at the range of 45-85° C., they are in equilibrium with each other. There are two reversible equilibrium reactions and an irreversible aromatization (cyclization) involved. The reactions finally push forward cyclization. Therefore, isolating the intermediate is not necessary and may incur additional cost and time in the preparation of the intermediate of formula VII. After the reaction, the crude formula VII can be directly isolated by filtration in high yield. However, inventors found that if N,N-dimethylformamide dimethylacetal (DMF-DMA) is far excessive with respect to formula VI, the aromatization (cyclization) would become slow and the isolated yield would be lower (see Table 3, entry 5 below). Preferably, the equivalent molar amount of formula VI relative to the molar amount of ortho-amino-benzonitrile derivative (Formula B) is 1.0-2.0, and the equivalent molar amount of N,N-dimethylformamide dimethylacetal (DMF-DMA) is 1.0-1.5 relative to the molar amount of ortho-amino-benzonitrile derivative (Formula B).

Scheme 8 - A one-step reaction for the preparation of the compound of formula VII

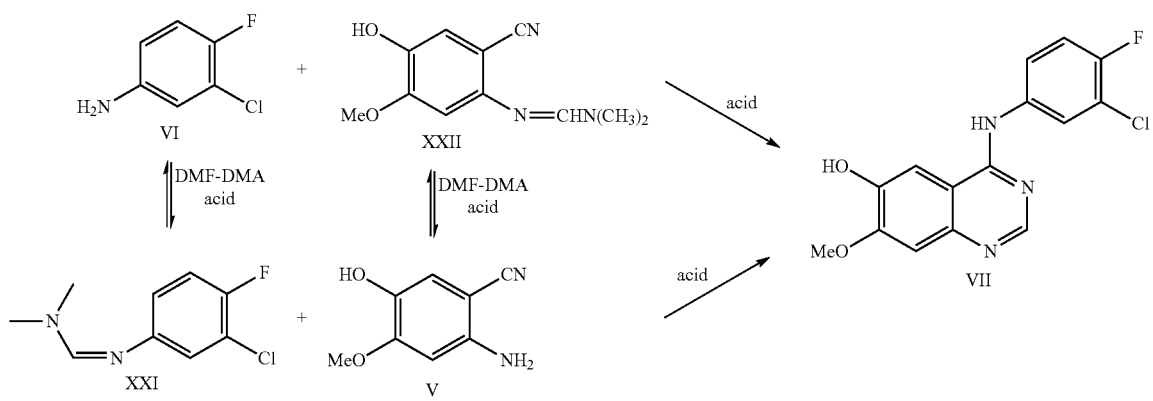

In accordance with yet another embodiment of the present application, the inventors found that different batches of crude formula VII were contaminated by different level of AcOH which would affect the next reaction. A crystallization from DMSO/water or DMSO/ACN could remove AcOH and give quite pure formula VII with 99% purity. Compared with DMSO/ACN, DMSO/water gives higher recovery yield (Example 3 and 4), the recovery yield is 95% and the total yield is 82% from formula V.

Formula VII after crystallization may be converted to gefitinib in DMF (6 vol. to 12 vol v/w, mL/g) in the presence of potassium carbonate. After the reaction is completed, either adding water to effect a precipitation or adding concentrated HCl (a.q.) to form a gefitinib hydrochloride salt is needed. Subsequently, the gefitinib hydrochloride salt can be converted to gefitinib (free base) by adjusting the pH value to 12-13 in a hot aqueous alkaline solution, and then crude gefitinib is obtained by filtration. Surprisingly, the inventors found that treating gefitinib hydrochloride salt with activated charcoal can more efficiently remove color in the water or the mixture of water and methanol, preferably the mixture of water and methanol, than treating gefitinib free base.

According to a further aspect of the present invention, crude gefitinib is crystallized from N-methyl-2-pyrrolidone (NMP), N,N-dimethyl acetamide (DMAC) or N,N-dimethylformamide (DMF)/aliphatic alcohol, or acetonitrile (ACN), preferably N-methyl-2-pyrrolidone (NMP)/iso propyl alcohol (IPA), NMP/ACN, or NMP/ACN/IPA, to afford gefitinib polymorph Form 1 disclosed in International Patent Application No. WO 03/072108. Generally, the more stable polymorphic form is the more suitable physical form for formulation and processing on a commercial scale. According to our study, only a single non-solvated gefitinib polymorph is the most stable, namely, gefitinib polymorph Form 1. Although WO 03/072108 discloses that Form 1 can be prepared by slurrying instable solvates, such as Form 2 MeOH solvate, Form 3 DMSO solvate and Form 5 trihydrate in ethyl acetate (EtOAc), and drying with warm nitrogen (60° C.), undoubtedly the most appropriate gefitinib polymorph for formulation is still gefitinib polymorph Form 1. Surprisingly, the inventors found that gefitinib polymorph form 1 can be crystallized by the use of a combination of N-methyl-2-pyrrolidone (NMP)/iso-propyl alcohol (IPA), NMP/acetonitrile (ACN), or NMP/IPA/ACN, and the crystallization can be apply to a large scale easily. In comparison with the conversion process as shown in WO 03/072108, the crystallization does not produce any instable solvates and just provides polymorph Form 1 directly. Therefore, it does not need any conversion processes to control polymorphic form on a large scale. As for Chinese Patent No. CN101973944, it provides a process for the preparation of polymorphic Form 1 by crystallization from ethanol, iso-propyl alcohol (IPA), n-butanol or combination thereof. However, gefitinib has a low solubility in ethanol, iso-propyl alcohol (IPA) and n-butanol, so a large volume of solvent is required. For the most recently published Chinese Patent Application No. CN103360326A, the crystallization process utilizing C2-C5 alcohol and some co-solvents provides gefitinib with 0.10% individual impurity. However, the inventors repeated several crystallization examples provided in the patent application and they found that the mixed solvents, such as ethanol/ethyl acetate (1:1, 10 vol), IPA/ACN (1:1, 10 vol.) and IPA/ACN (5:1, 15 vol.), cannot completely dissolve crude gefitinib as described in the examples. Therefore, a larger volume of the solvent mixture is required for the crystallization of gefitinib. Besides, it is non-logical that those examples show that the more solvent having relatively good solubility was used, the larger volume of mixed solvents was needed. By contrast, the present crystallization applies N-methyl-2-pyrrolidone (NMP) as a solvent having excellent solubility with gefitinib and iso-propyl alcohol (IPA) or acetonitrile as a co-solvent; it largely reduces the solvent volume in the purification of gefitinib.

According to a further aspect of the present application, a process for preparing the intermediate of formula X comprises conducting the amidine formation and cyclization steps in a one-step reaction. The advantage of the one-step reaction does not need to isolate any intermediates when involving the reaction of the compound of formula XXIII and 3-chloro-4-fluoroaniline (VI) in the preparation of the intermediate of formula X. Actually, several processes for preparing gefitinib are described in the literature, but those processes involve multiple steps and hence is consuming. The inventors of the present invention surprisingly noted that either between the compounds of formula VI and XXI or the compounds of formula V and XXIII, in the presence of a cyclization reagent N,N-dialkyl formamide acetal, e.g., N,N-Dimethylformamide Dimethylacetal (DMF-DMA), a Brønsted acid catalyst, e.g., acetic acid (AcOH) and trifluoroacetic acid (TFA), and a solvent, e.g., acetic acid (AcOH), toluene (PhMe), methanol (MeOH), acetonitrile (ACN), ethyl acetate (EtOAc), tetrahydrofuran (THF), N-methyl-2-pyrrolidone (NMP), and N,N-dimethylformamide (DMF), they are in equilibrium with each other. There are two reversible equilibrium reactions and an irreversible aromatization (cyclization) involved. The reactions finally push forward cyclization. Therefore, isolating the intermediate is not necessary and may incur additional cost and time in the preparation of the intermediate of formula X.

Scheme 9 A one-step reaction for the preparation of the compound of formula X

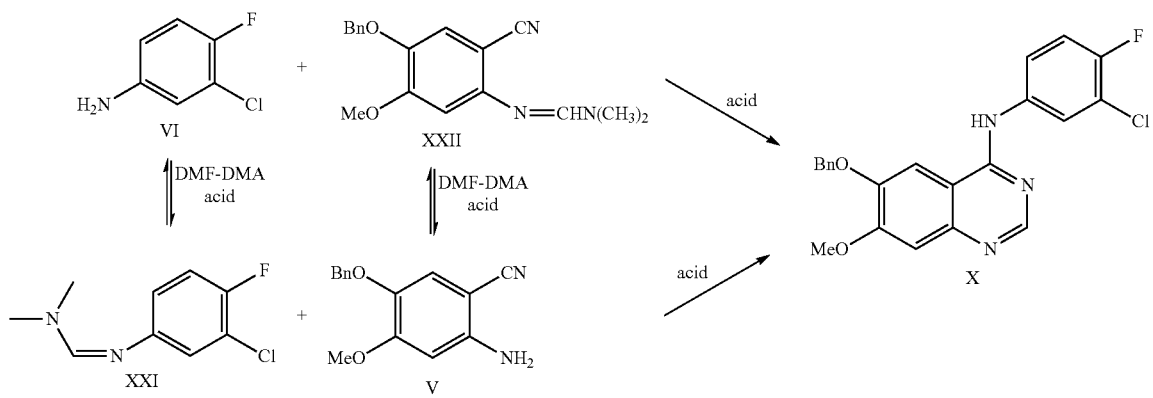

EXAMPLES

Example 1

Preparation of 4-[(3-chloro-4-fluorophenyl) amino]-7-methoxyquinazolin-6-ol (VII)

Under $N_2$, 2-amino-5-hydroxy-4-methoxybenzonitrile (V, 1.0 g, 6.1 mmol, 1.0 eq.), 3-chloro-4-fluoroaniline (VI, 0.90 g, 6.1 mmol, 1.0 eq.), N,N-dimethylformamide dimethylacetal (DMF-DMA, 0.73 g, 1.0 eq.) and acetic acid (AcOH, 8 mL, 8 P, v/wt) were heated to 80° C. for 18 h. After cooling, dichloromethane (DCM, 6 mL, 6 P) and water (2.5 mL, 2.5 P) was added to the mixture and stirred. The mixture was continued to cool in an ice-bath, pH adjusted to 8.0 with 20% aq. NaOH to effect precipitation and filtered. The solid was slurried in dichloromethane (DCM)/water, filtered, washed and dried to afford 4-[(3-chloro-4-fluorophenyl) amino]-7-methoxyquinazolin-6-ol (VII) in ca. 80% yield.

$^1$H NMR (400 MHz, d6-DMSO) δ 9.70 (s, 1H), 9.48 (s, 1H), 8.48 (s, 1H), 8.21 (dd, J=6.9, 2.7 Hz, 1H), 7.83 (m, 1H), 7.78 (s, 1H), 7.41 (t, 1H), 7.22 (s, 1H), 3.98 (s, 3H).

$^{13}$C NMR (100 MHz, d6-DMSO) δ 156.33, 154.41, 153.34 (J=241 Hz), 152.39, 147.23, 146.69, 137.65 (J=3 Hz), 123.24, 122.15 (J=7 Hz), 119.13 (J=18 Hz), 116.90 (J=21 Hz), 110.01, 107.66, 105.75, 56.40.

Example 2

Preparation of 4-[(3-chloro-4-fluorophenyl) amino]-7-methoxyquinazolin-6-ol (VII)

Under N2, 2-amino-5-hydroxy-4-methoxybenzonitrile (V, 200 g, 1.22 mol, 1.0 eq.), 3-chloro-4-fluoroaniline (VI, 212.8 g, 1.46 mol, 1.2 eq.), N,N-dimethylformamide dimethylacetal (DMF-DMA) (194 mL, 1.2 eq.), toluene (PhMe, 1.4 L) and AcOH (0.6 L) were heated to 65° C. for 6 h. The mixture was cooled to r.t., filtered, washed with acetonitrile (ACN, 400 mL) and dried in vacuo at 50° C. to afford crude formula VII (392.8 g) with 98.3% purity by HPLC.

TABLE 1

The comparison among different reaction solvent systems

| | | | | | | Crude VII | |
|---|---|---|---|---|---|---|---|
| Entry | V | VI | DMF-DMA | Solvent | Temp/Time | Purity | Yield |
| 1 | 1.0 eq. | 1.15 eq. | 1.15 eq. | MeOH/AcOH (7 P/3 P) | reflux/9.5 h | 92.9% | 69% |
| 2 | 1.0 eq. | 1.15 eq. | 1.15 eq. | EtOAc/AcOH (7 P/3 P) | reflux/9.5 h | 91.7% | 62% |
| 3 | 1.0 eq. | 1.15 eq. | 1.15 eq. | THF/AcOH (7 P/3 P) | reflux/14.0 h | 94.5% | 72.7% |
| 4 | 1.0 eq. | 1.15 eq. | 1.15 eq. | ACN/AcOH (7 P/3 P) | reflux/8.0 h | 96.7% | 79% |
| 5 | 1.0 eq. | 1.15 eq. | 1.15 eq. | PhMe/AcOH (8 P/ 2 P) | 55° C./10 h | 98.2% | 96% |

TABLE 2

The comparison among different reaction temperatures

| | | | | | | Crude VII | |
|---|---|---|---|---|---|---|---|
| Entry | V | VI | DMF-DMA | PhMe/AcOH | Temp/Time | Purity | Yield |
| 1 | 1.0 eq. | 1.15 eq. | 1.15 eq. | 7 P/3 P | 45° C./10 h | 97.8% | 85% |
| 2 | 1.0 eq. | 1.15 eq. | 1.15 eq. | 7 P/3 P | 45° C./10 h | 93.1% | 79% |
| 3 | 1.0 eq. | 1.2 eq. | 1.2 eq. | 7 P/3 P | 45° C./22 h | 95.1% | 92% |
| 4 | 1.0 eq. | 1.2 eq. | 1.2 eq. | 7 P/3 P | 55° C./10 h | 98.0% | 93% |
| 5 | 1.0 eq. | 1.2 eq. | 1.2 eq. | 7 P/3 P | 65° C./10 h | 98.4% | 96% |
| 6 | 1.0 eq. | 1.2 eq. | 1.2 eq. | 7 P/3 P | 75° C./4 h | 93.7% | 82% |
| 7 | 1.0 eq. | 1.2 eq. | 1.15 eq. | 7 P/3 P | 85° C./4 h | 95.9% | 79% |

TABLE 3

The effect of equivalents of VI and DMF-DMA

| | | | | | | Crude VII | |
|---|---|---|---|---|---|---|---|
| Entry | V | VI | DMF-DMA | PhMe/AcOH | Temp/Time | Purity | Yield |
| 1 | 1.0 eq. | 1.2 eq. | 1.2 eq. | 7 P/3 P | 65° C./10 h | 98.4% | 96% |
| 2 | 1.0 eq. | 1.5 eq. | 1.2 eq. | 7 P/3 P | 65° C./7 h | 98.8% | 86% |
| 3 | 1.0 eq. | 2.0 eq. | 1.2 eq. | 7 P/3 P | 65° C./7 h | 99.9% | 97% |
| 4 | 1.0 eq. | 1.2 eq. | 1.5 eq. | 7 P/3 P | 65° C./5 h | 97.1% | 92% |
| 5 | 1.0 eq. | 1.2 eq. | 2.0 eq. | 7 P/3 P | 65° C./5 h | 93.3% | 69% |

TABLE 4

The result of using TFA as an acidic catalysis

| Entry | V | VI | DMF-DMA | Acid | Solvent | Temp/Time | Conversion (by HPLC analysis) |
|---|---|---|---|---|---|---|---|
| 1 | 1.0 eq. | 1.1 eq. | 1.1 eq. | TFA (2.5 eq.) | DMF (5 P) | 65° C./24 h | 66.7% |
| 2 | 1.0 eq. | 1.1 eq. | 1.1 eq. | TFA (1.8 eq.) | PhMe/DMF (7 P/3 P) | 65° C./25 h | 67.1% |
| 3 | 1.0 eq. | 1.15 eq. | 1.15 eq. | TFA (3.0 eq.) | PhMe/NMP (7 P/3 P) | 65° C./7 h | 52.9% |

Example 3

Purification of Crude Formula VII

The crude formula VII (260 g, containing ca. 13.7% wt AcOH) from Example 2 was dissolved in dimethyl sulfoxide (DMSO, 2340 mL) at 100-105° C., the solution was cooled down to 90° C., and then the water (260 mL) was added dropwise to effect precipitation. The mixture was stirred at 90° C. for 1 h, then continued to cool to 20-25° C., water (520 mL) was added and stirred in an ice-water bath for 1 h. The mixture was filtered, washed and dried in vacuo at 50° C. to afford 212.4 g product with 99.7% purity. The yield was 82% from formula V.

Example 4

Purification of Crude Formula VII

The crude formula VII (20 g, containing ca. 13.7% wt AcOH) from Example 2 was dissolved in DMSO (180 mL) at 100-105° C., the solution was cooled down to 70° C., and then the ACN (160 mL) was added dropwise. The mixture was cooled to 20-25° C. and stirred in an ice-water bath for 1 h. The mixture was filtered, washed and dried in vacuo at 50° C. overnight to afford 15.2 g product with 99.7% purity. The yield was 74% from formula V.

Example 5

Preparation of N-(3-chloro-4-fluorophenyl)-7-methoxy-6-[3-(morpholin-4-yl)propoxy]quinazolin-4-amine (I, gefitinib)

Under $N_2$, the mixture of 4-[(3-chloro-4-fluorophenyl)amino]-7-methoxyquinazolin-6-ol (VII, 30.0 g, 93.8 mmol, 1.0 eq.), 4-(3-chloropropyl) morpholine (VIII, 16.1 g, 1.05 eq.), $K_2CO_3$ (25.9 g, 2.0 eq.) and N,N-dimethylformamide DMF (360 mL) was heated to 85° C. for 6 h. After the reaction completion, the mixture was cooled to 20-25° C. The mixture was filtered and washed with DMF (60 mL*2). The conc. HCl (3.0 eq.) was added dropwise into filtrate. A lot of solid precipitated. The mixture was filtered, washed with DMF (60 mL*2). The filter-cake was dissolved in water (360 mL) at 75° C. The 1N NaOH aq. was added to the mixture to adjust pH value about 12-13. The mixture was filtered, washed with $H_2O$ (60 mL*2) and dried in vacuo at 50° C. to afford gefitinib as off-white solid (38.0 g) with 96.7% purity in 87% yield.

$^1$H NMR (400 MHz, d6-DMSO) δ 9.44 (s, 1H), 8.50 (s, 1H), 8.12 (dd, J=6.9, 2.7 Hz, 1H), 7.80 (m, 2H), 7.44 (t, 1H), 7.20 (s, 1H), 4.18 (t, J=6.7 Hz, 2H), 3.94 (s, 3H), 3.59 (t, J=4.4 Hz, 4H), 2.49 (t, J=6.9 Hz, 2H), 2.41 (bs, 4H), 2.00 (m, 2H).

$^{13}$C NMR (100 MHz, $d_6$-DMSO) δ 156.48, 154.94, 153.57 (J=241 Hz), 153.05, 148.74, 147.43, 137.33 (J=3 Hz), 123.91, 122.77 (J=7 Hz), 119.19 (J=19 Hz), 116.90 (J=21 Hz), 109.26, 107.72, 103.14, 67.59, 66.43, 56.31, 55.35, 53.73, 26.13.

Example 6

Purification of Gefitinib

The crude gefitinib (34.3 g) from above Example 5 was dissolved in iso-propanol (IPA)/N-methyl-2-pyrrolidone (NMP) (4.37:1, v/v, 396.8 mL) at 80° C., the solution was cooled down to 62° C., solid precipitated and hold for 1 h at 62° C. The mixture was cooled to 20-25° C. and stirred in an ice-water bath for 1 h. The mixture was filtered, washed and dried in vacuo at 50° C. to afford 30.1 g polymorphic Form I product with 99.9% purity in 87% yield.

Example 7

Purification of Gefitinib

The crude gefitinib (6.0 g) and NMP (10.2 mL) were charged into a flask and heated to 80° C. until the mixture turned clear. Then ACN (12 mL) was added. The activated carbon (0.24 g, 4% wt.) was added and stirred at 80° C. for 1.0 h. The mixture was hot-filtered to remove activated carbon. ACN (60 mL) was added dropwise to the filtrate at 75° C. The mixture was cooled down to about 59° C., solid started to precipitate and hold for 1.0 h. After, the mixture was cooled to 25° C. Then the mixture was cooled in ice-water bath for 1.0 h. The mixture was filtered, washed with ACN (12 mL*2) and dried at 50° C. in vacuo to afford 5.2 g product with 99.9% purity in 86% yield.

Example 8

Preparation of Gefitinib

Under $N_2$, the mixture of 4-[(3-chloro-4-fluorophenyl)amino]-7-methoxyquinazolin-6-ol (VII, 70.0 g, 218.9 mmol, 1.0 eq.), 4-(3-chloropropyl) morpholine (37.6 g, 1.05 eq.), $K_2CO_3$ (36.3 g, 1.2 eq.) and DMF (360 mL, 6 P) was heated to 85° C. for 6 h. After the reaction completion, the mixture was cooled to 30±5° C. The mixture was filtered and washed with DMF (140 mL*2). The conc. HCl aq. (3.0 eq.) was added dropwise into filtrate. A lot of solid was precipitated and stirred for 1.0 h. The mixture was filtered, washed with ACN (140 mL*2). The filter-cake was dried at 50° C. in vacuo overnight to afford gefitinib hydrochloride salt (125 g).

Gefitinib hydrochloride salt (30.0 g) was dissolved in $H_2O$/MeOH (420 mL, v/v=7/7) at 65° C. The activated carbon (0.12 g, 4% wt.) was added to the mixture and stirred for 1.0 h. the mixture was hot-filtered. The 3N NaOH aq. was added to the mixture to adjust pH value about 12-13 and hold for 1.0 h at 65° C. The mixture was cooled down to 0-5° C. for 1.0 h. The mixture was filtered, washed with ACN (60 mL*2) and dried to afford crude gefitinib as off-white solid (19.8 g) with 96.7% purity.

Example 9

Purification of Gefitinib

The crude gefitinib (5 g) and NMP (10 mL) were charged into a flask and heated to 80° C. until the mixture turned clear. Then ACN (20 mL) was added. The activated carbon (0.4 g, 4% wt.) was added and stirred at 80° C. for 1.0 h. The mixture was hot-filtered to remove activated carbon. The mixture of IPA (30 mL) and ACN (10 mL) was added dropwise to the filtrate at 75° C. The mixture was cooled down to about 47° C., solid started to precipitate and hold for 1.0 h. After, the mixture was cooled to 25° C. Then the mixture was cooled in ice-water bath for 1.0 h. The mixture was filtered, washed with ACN (20 mL*2) and dried at 50° C. to afford product (3.75 g) with 99.9% purity in 75% yield.

Example 10

Preparation of 3-(benzyloxy)-4-methoxybenzonitrile (III)

Under $N_2$ (g), 3-hydroxy-4-methoxybenzonitrile (II, 10.0 g, 67.1 mmol, 1.0 eq.), benzyl bromide (BnBr, 9.7 mL, 1.2 eq.), potassium carbonate (11.1 g, 1.2 eq.) and methanol (MeOH, 50 mL, 5 P) were heated to reflux (ca. 65° C.) for 1.0 h. After the reaction completion by TLC analysis, the mixture was cooled to 25-30° C., diluted with dichloromethane (100 mL, 10 P), filtered and evaporated under vacuum at 35° C. to remove solvent. Water (50 mL) was added to the residue to effect precipitation. The solid was filtered, washed with water (30 mL×2), and dried in vacuo at 50° C. to give 15.0 g III in 93% yield.

$^1$H NMR (400 MHz, CDCl$_3$) δ 7.31-7.44 (m, 5H), 7.27 (dd, J=8.4, 2.0 Hz, 1H), 7.10 (d, J=2.0 Hz, 1H), 6.91 (d, J=8.4 Hz, 1H), 5.14 (s, 2H), 3.92 (s, 3H).

$^{13}$C NMR (100 MHz, CDCl$_3$) δ 153.57, 148.26, 135.91, 128.76 (2C), 128.31, 127.35 (2C), 126.87, 119.21, 116.48, 111.66, 103.76, 71.22, 56.12.

Example 11

Preparation of 5-(benzyloxy)-4-methoxy-2-nitrobenzonitrile (IV)

Under $N_2$ (g), HNO$_3$ (65%, 84 mL) was cooled to 0-5° C. To a solution of 3-(benzyloxy)-4-methoxybenzonitrile (III, 14.0 g, 58.6 mmol, 1.0 eq.) in acetic acid (33.6 mL, 2.4 P) was added dropwise at 0-10° C. and after the addition the temperature was allowed to warm to 20-25° C. After the reaction completion, ice-water (150 mL, 10.7 P) was added to the mixture. The mixture was filtered, washed with water (30 mL×2) and dried in vacuo at 50° C. to give desired 5-(benzyloxy)-4-methoxy-2-nitrobenzonitrile (IV, 13.5 g) in 85% yield.

$^1$H NMR (400 MHz, CDCl$_3$) δ 7.80 (s, 1H), 7.43-7.37 (m, 5H), 7.24 (s, 1H), 5.25 (s, 2H), 4.03 (s, 3H).

$^{13}$C NMR (100 MHz, CDCl$_3$) δ 152.70, 152.50, 142.91, 134.45, 129.00 (2C), 128.88, 127.47 (2C), 117.13, 115.50, 108.17, 100.65, 56.85.

Example 12

Preparation of 2-amino-5-hydroxy-4-methoxybenzonitrile (V)

10% of Pd/C (0.5 g, 10% wt.), methanol (MeOH, 125 mL, 25 P) and 5-(benzyloxy)-4-methoxy-2-nitrobenzonitrile (IV, 5.0 g, 17.6 mmol, 1.0 eq.) were charged into a high pressure hydrogenation reactor. The reaction was kept 2-3 atm at 20° C. for 1.5 h. After the reaction completion, the mixture was filtered to remove Pd/C and evaporated at 40° C. in vacuo to afford 2-amino-5-hydroxy-4-methoxybenzonitrile (V, 2.8 g) in 90% yield.

$^1$H NMR (400 MHz, d$_6$-DMSO) δ 8.58 (s, 1H, exchangeable), 6.65 (s, 1H), 6.37 (s, 1H), 5.41 (s, 2H, exchangeable), 3.73 (s, 3H).

$^{13}$C NMR (100 MHz, d$_6$-DMSO) δ 154.05, 147.48, 138.05, 119.17, 116.66, 99.49, 84.63, 55.75.

Example 13

Preparation of 2-amino-5-(benzyloxy)-4-methoxybenzonitrile (IX)

Under $N_2$, a stirring of mixture of 5-(benzyloxy)-4-methoxy-2-nitrobenzonitrile (IV, 10.0 g, 35.2 mmol, 1.0 eq.), tetra-n-butylammonium bromide (TBAB, 0.94 g, 0.085 eq.), sodium dithionite (Na$_2$S$_2$O$_4$, 19.0 g, 3.1 eq.) in methanol (MeOH)/H$_2$O (200 mL, 1:1, v/v) was heated 30° C. The reaction was monitored by TLC. Upon completion of the reaction, then hydrochloric acid (20 mL) was added and stirred for 1.0 h. The mixture was extracted with dichloromethane (DCM). The organic phase was evaporated in vacuum at 25° C. to give 2-amino-5-(benzyloxy)-4-methoxybenzonitrile.

$^1$H NMR (400 MHz, CDCl$_3$) δ 7.41-7.30 (m, 5H), 6.83 (s, 1H), 6.24 (s, 1H), 5.02 (s, 2H), 4.18 (s, 2H, exchangeable), 3.87 (s, 3H).

$^{13}$C NMR (100 MHz, d$_6$-DMSO) δ 155.42, 149.16, 139.46, 137.60, 128.79 (2C), 128.33 (2C), 128.28, 119.08, 116.92, 99.45, 84.03, 71.38, 55.87.

Example 14

Preparation of 6-(benzyloxy)-4-(3-chloro-4-fluorophenylamino)-7-methoxyquinazoline (X)

Under $N_2$, 2-amino-5-(benzyloxy)-4-methoxybenzonitrile (IX, 2.6 g, 8.4 mmol, 1.0 eq.), 4-(3-chloropropyl)morpholine (VIII, 1.47 g, 10.1 mmol, 1.2 eq.), N,N-dimethylformamide dimethylacetal (DMF-DMA, 1.0 g, 1.0 eq.) and acetic acid (AcOH, 10.4 mL, 4 P) were charged into a flask and heated to 110° C. The reaction was monitored by TLC. Upon completion of the reaction, the reaction mixture was cooled to r.t. Water (15.6 mL, 6 P) and dichloromethane (6.5 mL, 2.5 P) was added and stirred. The mixture was pH adjusted to 8~9 by 6 N aq. KOH. A lot of solid precipitated, filtered, washed and dried to afford 2.0 g solid Formula X in about 60% yield.

$^1$H NMR (400 MHz, d6-DMSO) δ 9.61 (s, 1H), 8.52 (s, 1H), δ 8.16 (dd, J=2.70 Hz, 1H), 8.01 (s, 1H), 7.82 (m, 1H), 7.57-7.40 (m, 6H), 7.24 (s, 1H), 5.24 (s, 2H), 3.94 (s, 3H).

$^{13}$C NMR (100 MHz, d$_6$-DMSO) δ 156.52, 155.01, 153.58 (J=241 Hz), 153.20, 148.52, 147.59, 137.34, 136.74, 129.01 (2C), 128.81 (2C), 128.70, 123.79, 122.62 (J=7 Hz), 119.25 (J=18 Hz), 116.96 (J=22 Hz), 109.21, 107.86, 103.54, 71.11, 56.34.

Example 15

Preparation of 4-(3-chloro-4-fluorophenylamino)-7-methoxyquinazolin-6-ol (VII)

Under N2, 6-(benzyloxy)-4-(3-chloro-4-fluorophenylamino)-7-methoxyquinazoline (X, 3 g, 7.3 mmol, 1.0 eq.) and anisole (15.8 mL) in trifluoroacetic acid (TFA, 60 mL, 20 P) was heated at 75° C. for 4 h. The mixture was cooled to r.t. and pH adjusted to 6-7 to effect precipitation. The solid was filtered, washed with water and acetonitrile, and dried in vacuo to give Formula VII with 95% purity in 90% yield.

What is claimed is:

1. A process of making a compound of formula A:

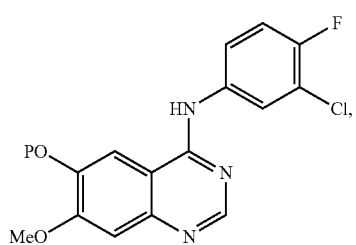

wherein P is hydrogen, 3-(morpholinyl)propyl, or a hydroxyl-protecting group, comprising reacting a compound of formula B or its salt:

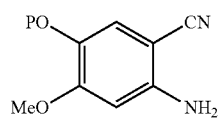

with 3-chloro-4-fluoroaniline (VI) in the presence of a N,N-dialkyl formamide acetal, a Bronsted acid catalyst and a solvent.

2. The process of claim 1, wherein said N,N-dialkyl formamide acetal is N,N-dimethylformamide dimethylacetal (DMF-DMA).

3. The process of claim 1, wherein the Bronsted acid catalyst is acetic acid (AcOH) or trifluoroacetic acid (TFA).

4. The process of claim 1, wherein the solvent is selected from the group consisting of AcOH, toluene (PhMe), methanol (MeOH), acetonitrile (ACN), ethyl acetate (EtOAc), tetrahydrofuran (THF), N-methyl-2-pyrrolidone (NMP), N,N-dimethylformamide (DMF), and combinations thereof.

5. The process of claim 4, wherein the solvent is the mixture of AcOH and toluene (PhMe).

6. The process of claim 1, wherein the reacting is performed at a temperature of 20-100° C.

7. The process of claim 1, wherein the molar equivalents of formula VI and N,N-Dimethylformamide Dimethylacetal (DMF-DMA) are about 1-2 and 1-1.5, respectively, relative to the molar amount of the compound of formula B.

8. The process of claim 1, wherein the compound of formula A is crystallized from a mixture of dimethyl sulfoxide and water (DMSO/H$_2$O) or dimethyl sulfoxide and acetonitrile (DMSO/ACN).

9. A process of making gefitinib or a pharmaceutically acceptable salt thereof comprising:
reacting a compound of Formula V:

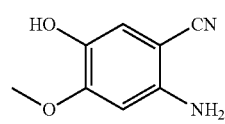

or its salt with 3-chloro-4-fluoroaniline (VI) in the presence of a N,N-dialkyl formamide acetal, a Brønsted acid catalyst, and a solvent to prepare a compound of formula VII:

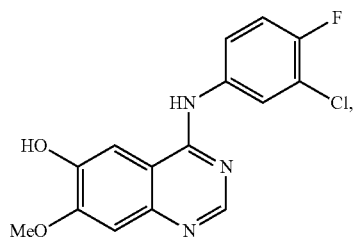

and
converting the compound of formula VII to gefitinib or its pharmaceutically acceptable salt thereof.

10. The process of claim 9 wherein the step of converting comprises reacting the compound of formula VII with 4-(3-chloropropyl)morpholine (VIII) to form gefitinib.

11. The process of claim 9 further comprising:
isolating gefitinib from a reaction mixture obtained in the converting step to obtain crude solid gefitinib;
dissolving crude solid gefitinib in a first solvent selected from the group consisting of N-methyl-2-pyrrolidone (NMP), N,N-dimethyl acetamide (DMAC), N,N-dimethylformamide (DMF), and combinations thereof to obtain a solution;
forming crystals by adding a second solvent selected from the group consisting of a C$_1$-C$_4$ aliphatic alcohol, acetonitrile (ACN), and combination thereof into the solution.

12. The process of claim 11 wherein the first solvent is N-methyl-2-pyrrolidone (NMP), and the second solvent is isopropyl alcohol (IPA), acetonitrile (ACN), or a mixture of isopropyl alcohol (IPA) and acetonitrile (ACN).

13. The process of claim 11 wherein the dissolving is conducted at a temperature of 70-100° C.

* * * * *